(12) United States Patent
Binder et al.

(10) Patent No.: US 9,375,238 B2
(45) Date of Patent: Jun. 28, 2016

(54) ROTATABLE BONE PLATE

(75) Inventors: Lawrence Binder, Doylestown, PA (US); Steven Ludwig, Baltimore, MD (US)

(73) Assignee: Globus Medical, Inc., Audubon, PA (US)

( * ) Notice: Subject to any disclaimer, the term of this patent is extended or adjusted under 35 U.S.C. 154(b) by 119 days.

(21) Appl. No.: 13/271,422

(22) Filed: Oct. 12, 2011

(65) Prior Publication Data

US 2012/0089189 A1  Apr. 12, 2012

Related U.S. Application Data

(62) Division of application No. 11/550,704, filed on Oct. 18, 2006, now Pat. No. 8,062,341.

(51) Int. Cl.
*A61B 17/80* (2006.01)
*A61B 17/70* (2006.01)

(52) U.S. Cl.
CPC .......... *A61B 17/7059* (2013.01); *A61B 17/701* (2013.01); *A61B 17/7007* (2013.01); *A61B 17/7011* (2013.01); *A61B 17/7032* (2013.01); *A61B 17/7044* (2013.01)

(58) Field of Classification Search
CPC .......... A61B 17/7002; A61B 17/7041; A61B 17/7044
USPC .......... 606/70–71, 246–299; 623/17.11–17.16
See application file for complete search history.

(56) References Cited

U.S. PATENT DOCUMENTS

| 6,648,885 | B1 * | 11/2003 | Friesem ........................ 606/278 |
| 2004/0153070 | A1 * | 8/2004 | Barker et al. ................... 606/61 |
| 2006/0149252 | A1 * | 7/2006 | Markworth et al. ............. 606/69 |
| 2007/0118121 | A1 * | 5/2007 | Purcell et al. ................... 606/61 |
| 2008/0086124 | A1 * | 4/2008 | Forton et al. .................... 606/60 |

* cited by examiner

*Primary Examiner* — Matthew Lawson

(57) ABSTRACT

The present invention relates generally to a bone plate for stabilizing bony structures. More particularly, the invention is directed to bone plates having an elongate body to which an integrated rod is formed. Integrated rod portion may be captured by a bone anchor with a receiving member. The bone plate is movable from a first position to a second position and may have an aperture for lagging the bone plate to the bone.

20 Claims, 12 Drawing Sheets

ROTATABLE BONE PLATE

CROSS REFERENCE TO RELATED APPLICATIONS

This application is a divisional application of U.S. patent application Ser. No. 11/550,704 filed on Oct. 18, 2006 now U.S. Pat. No. 8,062,341, which is incorporated by reference in its entirety herein.

FIELD OF THE INVENTION

The present invention relates to a bone fixation plate used to stabilize vertebrae and other bony anatomy. More specifically, the present invention relates to a bone plate having a minimized profile that easily and reliably aids in spinal fusion techniques.

BACKGROUND OF THE INVENTION

Bones and bony structures are susceptible to a variety of weaknesses that can affect their ability to provide support and structure. Weaknesses in bony structures may have many causes, including degenerative diseases, tumors, fractures, and dislocations. Advances in medicine and engineering have provided doctors with a plurality of devices and techniques for alleviating or curing these weaknesses.

The cervical spine has presented the most challenges for doctors, partially due to the small size of the vertebrae and the spacing between adjacent vertebrae. Even throughout the spine, because of its proximity to the spinal nerve and the importance the spine plays in day-to-day activities, correcting spinal disorders requires reliable and effective treatments.

Typically, weaknesses in the spine are corrected using devices that fuse one or more vertebrae together. Several artificial materials and implants have been developed to replace the vertebral body, such as, for example, titanium cages, ceramic, ceramic/glass, plastic or PEEK, and carbon fiber spacers. Recently, various expandable prosthetics or expandable cages have been developed and used for vertebral body replacement or in conjunction with other fusion procedures.

During fusion or other corrective procedures, bone plates or other stabilization systems are used to help maintain rigidity of the treated area, maintain compression between adjacent vertebrae, and fix or stabilize the area being fused. One such example is disclosed in U.S. patent application Ser. No. 11/464,625, which is incorporated herein by reference. Thus the bone plate is attached to two vertebrae to secure the area of fusion. As plates are often constructed of a single material, they are stable, strong devices.

In other instances, staples, anchors, and rod assemblies are used to stabilize the area being fused. Under these procedures, staples are placed into the adjacent vertebra with anchors. Titanium rods may then be fixed to the staple/anchor assemblies. One such system is disclosed in U.S. Pat. No. 6,986,771, which is incorporated herein by reference. Stabilization techniques involving rods allow for customization during implantation and a greater degree of control over placement, tension, load, and other important characteristics known to those of skill in the art.

Design considerations for fixation systems include ease of use, stability, ability of the surgeon to customize during implantation, and ability of the fixation system to allow for compression. Past fixation system designs have not necessarily alleviated all of the problems. Accordingly, a need exists for fixation systems that can provide a surgeon and patient with stable, customizable fixation systems.

SUMMARY OF THE INVENTION

The present invention relates to a fixation system used in spinal procedures. More particularly, a fixation system that has a hybrid attachment mechanism that provides a surgeon with greater flexibility during a fusion procedure is provided.

In an embodiment of the present invention, a bone plate is provided comprising an elongate plate body having a longitudinal axis and the plate body further comprising an integrated rod portion configured for attachment to a receiving member of a first bone fastener. The bone plate further has an aperture configured to receive a second bone fastener. The bone plate is capturable by the receiving member of the first bone fastener and movable from a first position to a second position. The rotatable bone plate is configured to be locked in a second position to stabilize bony structure.

DETAILED DESCRIPTION OF THE PREFERRED EMBODIMENTS

The present invention relates to a bone fixation plate that minimizes the problems associated with prior bone fixation plates while maintaining a small profile.

The invention is directed to bone stabilization plates for attachment to bony structures. Throughout the application, reference may be made to bony structures. Without limiting the term, bony structures refers to any bony or bone-like tissue in a mammalian body. The bone plate is generally rectangular in shape with a longitudinal axis extending from a first end to a second end. The bone plate is attachable to bony structures and reference will be made to attachment points, with each end of the bone plate configured for attachment to bony structures. For the sake of convenience, reference throughout the specification will be made to a first attachment point and second attachment point on one or more bony structures. A first end of the bone plate will generally be attachable to a first attachment point and a second end of the bone plate will generally be attachable to a second attachment point.

In one embodiment, the bone fixation system is a plate that has an integrated rod and an aperture. In this embodiment, a first end of the bone plate has an integrated rod portion; the second end of the bone plate as an aperture. The integrated rod may be captured by a bone fastener and the bone fastener's receiving member. In this embodiment, a bone fastener is inserted into a first attachment point in a bony structure. Upon capture of the integrated rod portion by the receiving member of the bone fastener, the plate is configured to be movable from a first position to a second position. The first position may be one in which a surgeon has greater access or view into the treated area of the spine. In the second position, the plate is aligned with the bony structures to provide maximal stabilization. In most cases, this means the lower surface of the bone plate is adjacent or on top of the bony surfaces being stabilized.

Once in the second position, the bone plate may be locked into position. In this embodiment, a second bone fastener may be driven through the aperture located on the second end of the bone plate to lag the bone plate to the bone. The integrated rod, which has been captured by the other bone fastener and its receiving member may be then be locked using a set screw or other locking member so that the integrated rod is no longer capable of being moved or rotated. As one of skill in the art would understand, prior to locking the integrated rod, the bony structure may be distracted or compressed.

Figure 1:
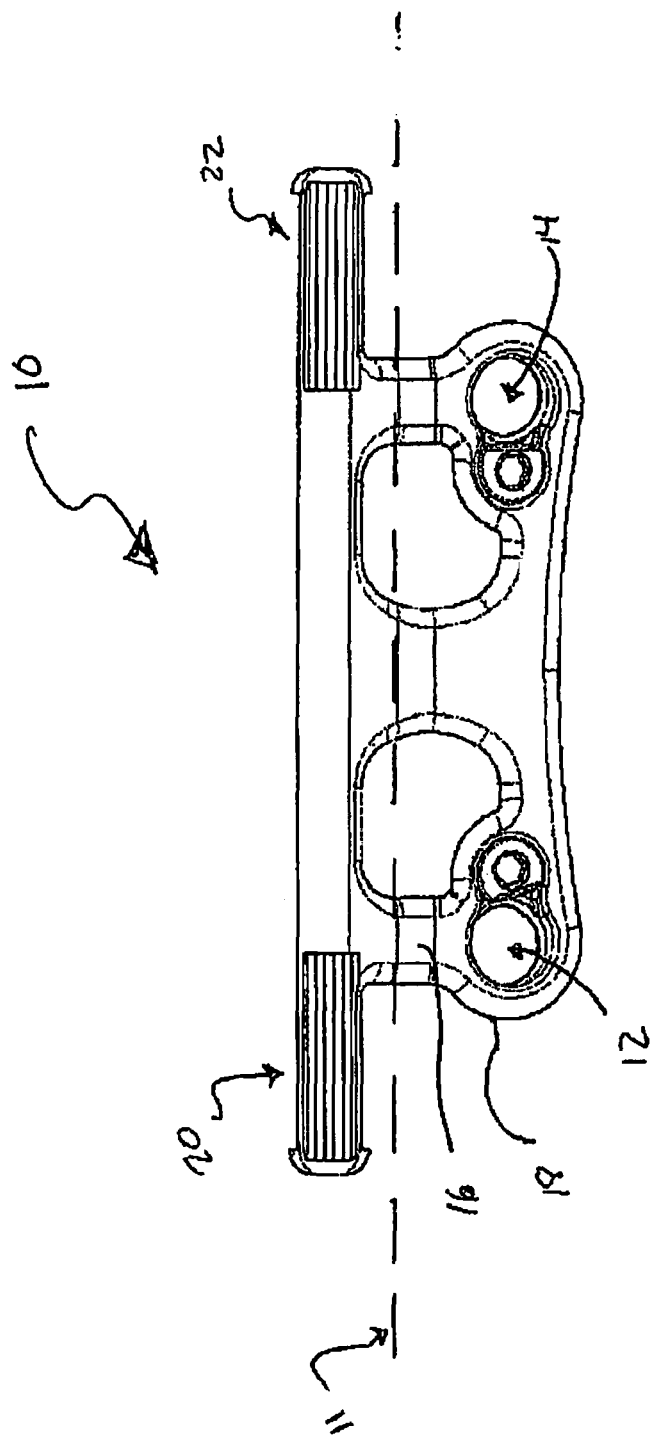
FIG. 1 is an isometric view of a bone plate of an embodiment of the present invention.

Referring now to FIG. 1, an alternative embodiment of the present invention is shown. In FIG. 1 a bone plate assembly 10 is provided. As seen in FIG. 1, bone plate assembly 10 is generally rectangular in shape, has a longitudinal axis 11, and has two apertures 12, 14 extending through upper surface 16 to lower surface 18. Apertures 12, 14 are configured to receive bone fasteners for anchoring the plate to bone and are located at each end of bone plate 10.

As further seen in FIG. 1, bone plate assembly 10 has a length over which bone plate 10 will stabilize bony structure, which in some instances may be two separate bony structures. Thus, aperture 12 may be used to anchor bone plate assembly 10 to a first bony structure while aperture 14 may anchor plate 10 to a bony structure. As seen in FIG. 1, bone plate 10 further has integrated rod portions 20 and 22. Integrated rod portions 20 and 22 are generally cylindrical in shape and extend longitudinally substantially parallel to longitudinal axis 11. Bone plate 10 has integrated rod portions 20 and 22 located at a first and second end of bone plate 10, respectively.

Figure 2:
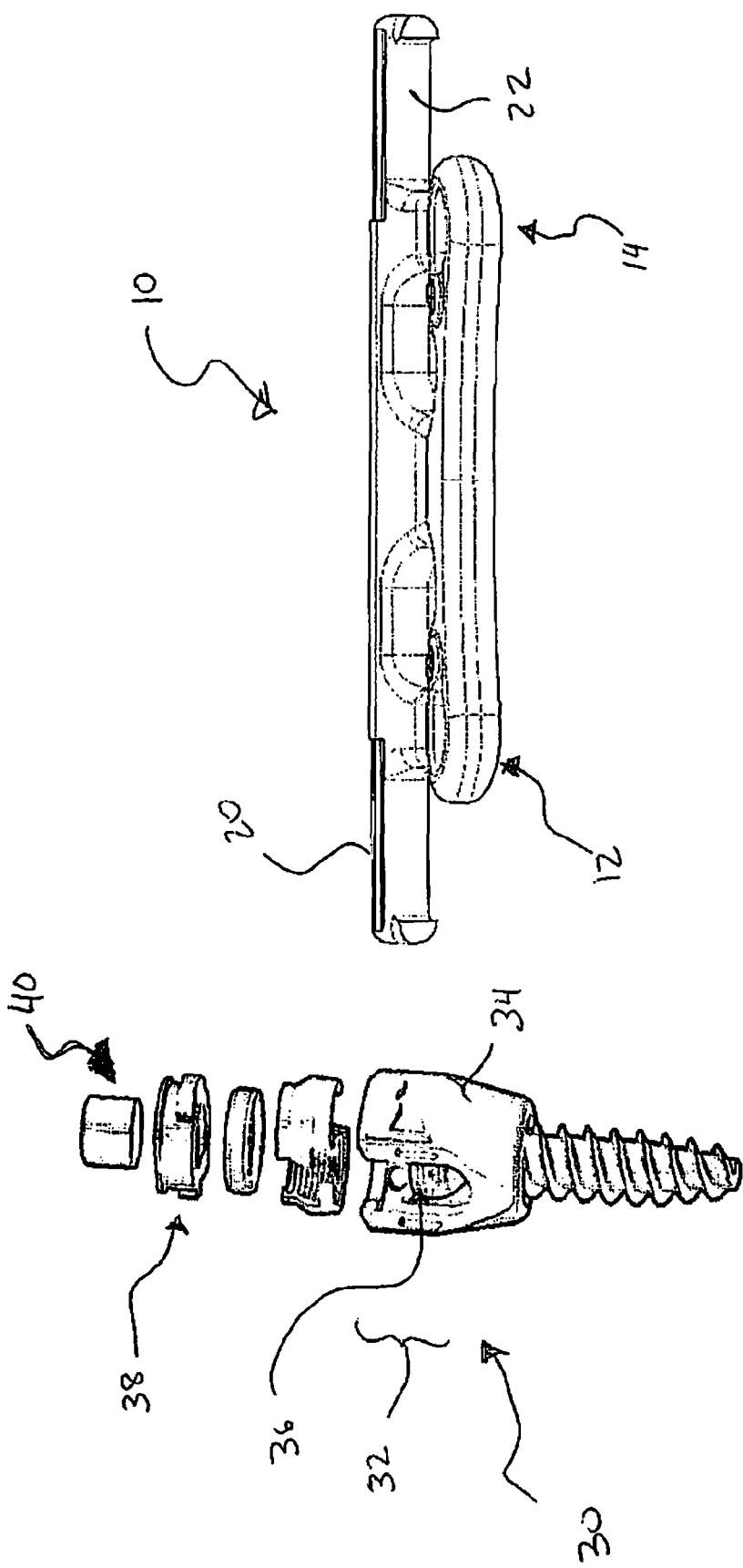
FIG. 2 is a perspective view of the bone plate of FIG. 1 and a bone fastener with receiving member.

With reference to FIG. 2 the bone plate assembly 10 is shown in profile view. Also shown in FIG. 2 is bone fastener 30. The present invention contemplates using bone fasteners of various types known to those of skill in the art. In a particular embodiment, bone fastener 30 has a receiving member 32 comprised of a body 34 in which elongate slot 36 is formed, creating a U-shaped channel in body 34. As one of skill in the art would understand, body 34 of receiving member 32 is configured to receive integrated rod portion 20, which in turn captures bone plate assembly 10.

As further seen in FIG. 2, fastener 30 has cap 38 that is used to help capture integrated rod portion 20. Thus, once integrated rod portion 20 is seated in slot 36, cap 38 is placed into receiving member 32 and rotated to capture integrated rod portion 20. While captured, integrated rod portion 20 (an in turn bone plate assembly 10) is able to rotate or otherwise be positionable with respect to the anchored bone fastener 30. By only capturing bone plate assembly 10, bone plate 10 is able to be moved and/or rotated while captured.

After bone plate 10 has been captured and moved to a desired position or the surgeon has treated the appropriate area as described in more detail below, the bone plate may be rotated into a second position. In this position the lower surface of the bone plate is generally aligned with the bony structure(s) the bone plate is stabilizing. After finalizing the position, the position of the bone plate may be fixed by locking the integrated rod portion to the bone fastener. In this particular embodiment, set screw 40 is used to lock integrated rod portion 20 to the bone fastener 30. Thus, once captured and rotated into a final position, set screw 40 is inserted into cap 38 of fastener 30. As set screw 40 is inserted, it will begin to clamp down on integrated rod portion 20. The upward forces of the assembly are counteracted by the interaction between cap 38 and body 34 of the receiving member 32. Thus, as the set screw is tightened, elongate rod 20 is locked into position relative to bone fastener 30.

As one of skill in the art would understand, the specifics of the capture mechanism and fastener may differ. Thus for example, the fasteners used to capture the integrated rod portion may be monoaxial or polyaxial. Furthermore, the fasteners may be bicortical fasteners or other fasteners. Or the fasteners may be cannulated or not. The present invention is not limited to any particular fastener but merely directed to a bone plate system in which a bone fastener is able to receive an integrated rod portion of a bone plate assembly. Thus, the particular capture mechanism and locking mechanism of the bone fastener is not material to the present invention.

As one of skill in the art would understand, a similar fastener may be used to capture integrated rod 22 of bone plate 10. And as described in more detail below, both integrated rod portions 20 and 22 may be captured during implantation of the bone plate assembly 10. Thus, two bone fasteners may be inserted into two separate bone structures with each bone fastener capturing an integrated rod portion of the bone plate. This configuration allows for the initial positioning of the bone plate assembly. Furthermore, the initial positioning (and capture) of the bone plate may occur in a first position, wherein the bone plate is orientated to provide the surgeon with maximum visibility or access.

As further seen in FIGS. 1 and 2, apertures 12 and 14 are configured to accept bone plate fasteners (not shown). As one of skill in the art would understand, bone plate fasteners are used to lag the plate to the bone and secure the position of the bone plate to the bony structures. While any number of different bones fasteners may be used, typically the apertures are configured such that at the lower surface of the bone plate, interference between the head of the fastener and the bone plate allows the fastener to lag the plate to the bone. While not specifically shown, various locking elements or retaining elements may be used to prevent the back out of the bone fastener. Thus, after positioning the bone plate assembly in a second position, the surgeon may insert bone screws into the apertures to lag the bone plate to the bone.

Figure 3:
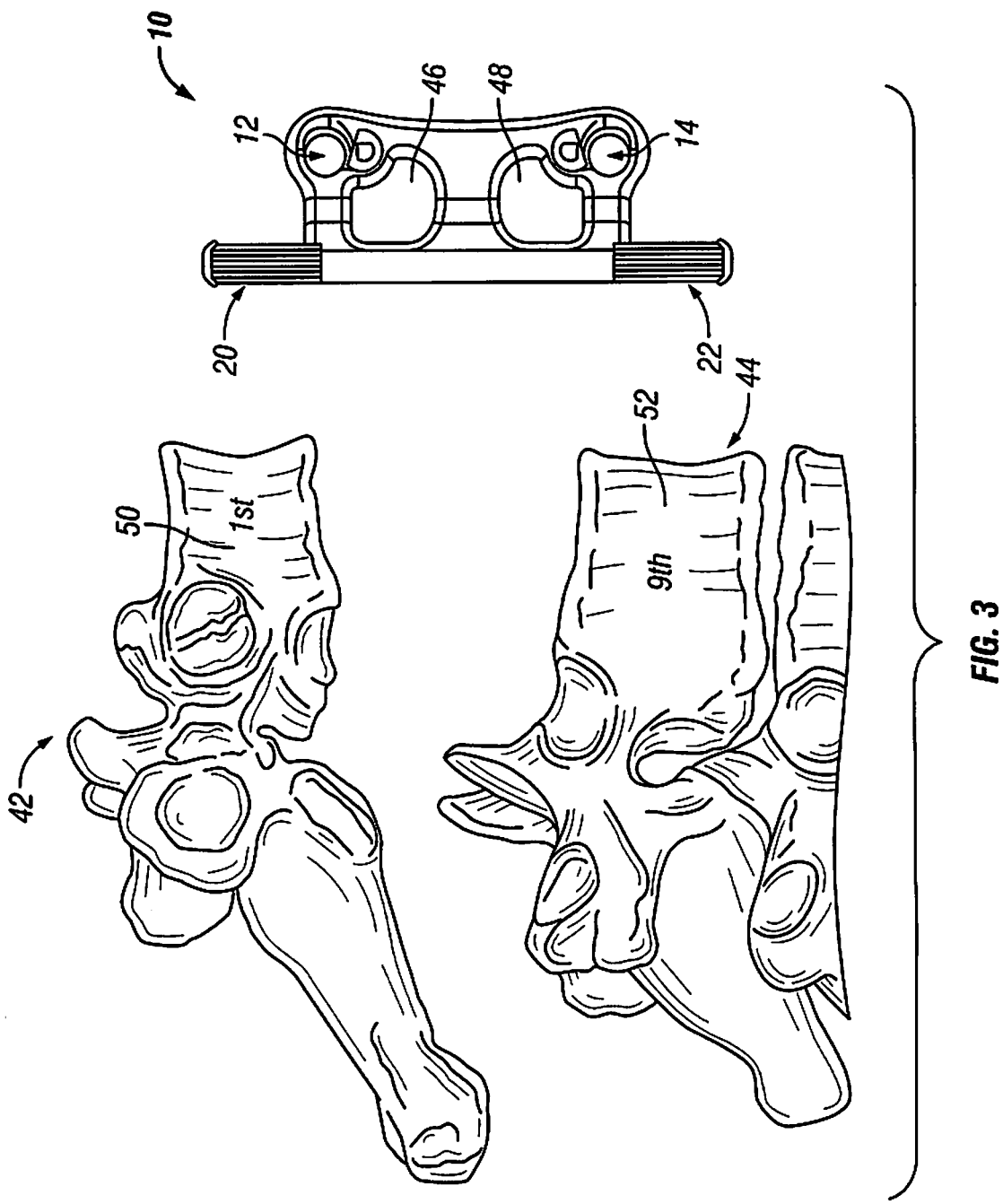
FIG. 3 is a perspective view of the bone plate of FIG. 1 in relation to illustrations of vertebral bodies.

With reference to FIG. 3, an embodiment of bone plate 10 is shown in relation to vertebral body bony structures 42 and 44. As seen in FIG. 3, a representative area of the spine is illustrated showing a missing vertebral body. Such an instance may occur during a corpectomy, which refers to the excision of a vertebral body. Typically, the procedure is accompanied by the interposition of a prosthesis, bone graft, or other stabilizing structure. In addition, corpectomies often use the aid of bone plates to (a) further stabilize the treated area and (b) act as a guard against the dislodgment of the interposed stabilization device.

Returning to FIG. 3, a portion of the spine is shown with a vertebral body missing between vertebral bodies 42 and 44. While not shown, a stabilization structure such as a corpectomy cage or other device may be inserted between vertebral bodies 42 and 44 to stabilize the spine and maintain proper spacing. As seen in FIG. 3, bone plate 10 has a length L configured to span vertebral bodies 42 and 44. As further seen in FIG. 3, bone plate 10 is configured such that the integrated rod portions 20, 22 and apertures 12, 14 overlap with vertebral bodies 42 and 44 to allow attachment of the bone plate to the bony structures.

As one of skill in the art would understand, bone plate 10 is also configured with windows 46 and 48. Windows 46 and 48 are oversized apertures that extend through upper surface 16 to lower surface 18 of bone plate 10. Windows 46 and 48 are configured to provide a surgeon with a view to the treated area when bone plate 10 is in a second position. Windows 46 and 48 are further configured to maintain the structural stability of bone plate 10 yet provide a direct visual line of site to the treated area without affecting the rigidity of bone plate 10.

With continuing reference to FIG. 3, bone fasteners with receiving members may be anchored into vertebras 42 and 44 at a first attachment point and second attachment point, respectively. Upon capture of integrated rod portions 20 and 22 by receiving members 32 of bone fasteners 30, bone plate 10 may be rotated into a second position. In the second position, first end and second end portions of bone plate 10 are disposed adjacent the bony surface of vertebras 42 and 44. In this manner, lower surface 18 of first end and second end portions of bone plate 10 may come into contact with bony surfaces 50 and 52 of vertebral bodies 42 and 44. This configuration provides stability and added rigidity to the fully implanted construct.

Furthermore, upon rotation of bone plate 10 into a second position, bone anchors may be inserted through apertures 12 and 14 to lag bone plate 10 to vertebral bodies 42 and 44. Before or prior to lagging the bone plate, the integrated rod portions may be locked to the receiving members and bone fastener. Whether one or more of the integrated rod is locked depends on user preference and whether additional distraction or compression is desired.

For example, one feature of the bone plate is the ability to compress or distract the bone plate after initial placement. Thus in one embodiment using the bone plate of FIG. 1, a surgeon may: (a) insert bone anchors with receiving members at a first attachment point and second attachment point, (b) place the integrated rod portions of the bone plate into the receiving members of implanted bone anchors, (c) capture the integrated rod portions, (d) rotate the bone plate into a second position, (e) place a third bone anchor through a first aperture lagging the bone plate to one of the bony structures, (f) lock the integrated rod portion on the end portion of the bone plate in which the third bone anchor was placed, (g) distract or compress the partially stabilized bony structures, (h) lock the remaining integrated rod portion, and then (i) insert a fourth bone anchor into the remaining aperture to finalize the position of the bone plate.

Another feature of the bone plate is the ability of the surgeon to make an initial placement of the bone plate before, during, or after treating the area to be treated. Thus in one embodiment, after a corpectomy the surgeon may place the bone plate in position by capturing the bone plate using bone anchors with receiving members and capturing the integrated rod portion of a bone plate. Because of the ability to rotate the bone plate in a position that provides access to the underlying area, the surgeon may treat the area, whether by inserting a stabilizing structure or making adjustments to a previously inserted stabilizing structure. Once complete, the surgeon may rotate the plate into a second position, compress or distract according to needs, and finalize the bone plate's position. Upon finalizing the bone plate position, the bone plate serves to stabilize the treated area.

As one of skill in the art would understand, various modifications to the steps of implanting the bone plate could be made depending on the precise configuration of the bone plate. Thus, for example, using the bone plate of FIG. 1 a surgeon may prefer to capture only one integrated rod portion and leave the other free until finalizing the position. In another variation, the surgeon may lock one integrated rod portion to conduct compression or distraction on the treated area (rather than using a bone anchor through an aperture to fix the plate to one of the bony structures). In another embodiment, both integrated rod portions are captured and distraction or compression occurs without additional bone anchors or locking the integrated rod portions. In this embodiment, once the bone plate is in a final position, the bone plate may be locked by either locking both integrated rod portions or locking an integrated rod portion on a first end and lagging the bone plate to bone using a bone anchor through an aperture on a second end.

Figure 4:
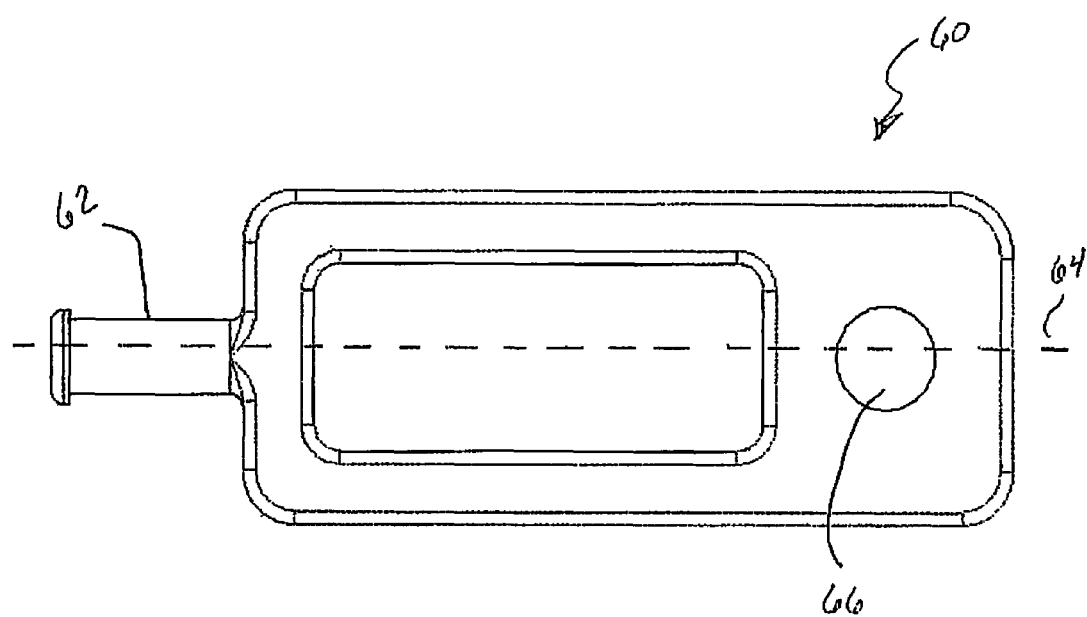
FIG. 4 is an exemplary embodiment of a bone plate of the present invention.

In alternative embodiments, the bone plate may have an integrated rod in different configurations that allows the bone plate to pivot from a first position to a second position. For example, as seen in FIG. 4 bone plate 60 may be configured with one integrated rod 62 at a first end extending parallel to longitudinal axis 64 of bone plate 60. Integrated rod 62 may be attached to a first attachment point on a bony structure using a bone fastener with a receiving member as described previously. At a second end of bone plate 60, bone plate 60 has aperture 66 for receiving a second bone fastener and attachment of the bone plate at a second attachment point. Second bone fastener is used to lag bone plate 60 to bony structure. The configuration described permits capture of the bone plate during implantation using integrated rod 62. Thus, as described previously, the configuration illustrated in FIG. 4 allows bone plate 60 to rotate from a first position to a second position. Furthermore, as one of skill in the art would understand, bone plate 60 allows for modifying the position of the bone and other procedures, such as compression and distraction, while the bone plate is in a second portion.

Figure 5:
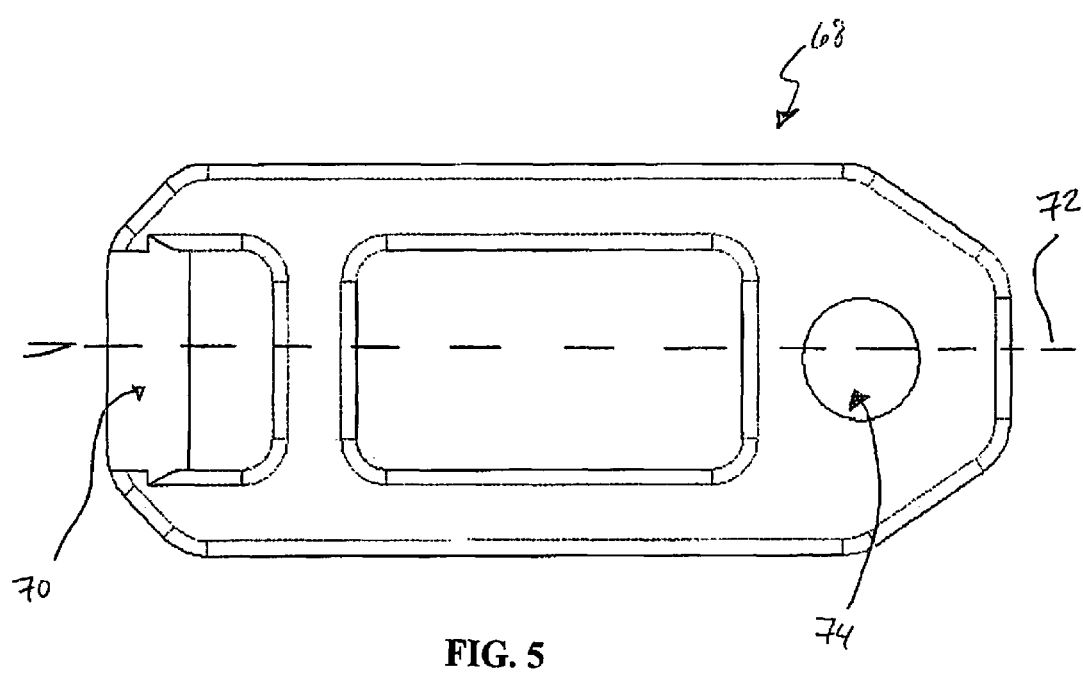
FIG. 5 is an exemplary embodiment of a bone plate of the present invention.

In alternative embodiments as seen in FIG. 5, bone plate 68 may have integrated rod portion 70 extend perpendicular to longitudinal axis 72 of bone plate 68. The bone plate in this configuration may have any number of apertures and is not limited to having the single aperture 74 illustrated. As one of skill in the art would understand, the configuration of bone plate 68 permits initial capture of the bone plate using integrated rod portion 70 by a bone fastener with a receiving member. After capture, the bone plate may be rotated from a first position to a second position. Furthermore, as described previously the bone plate is capable of compression and distraction in a captured, but unlocked position.

Figure 6:
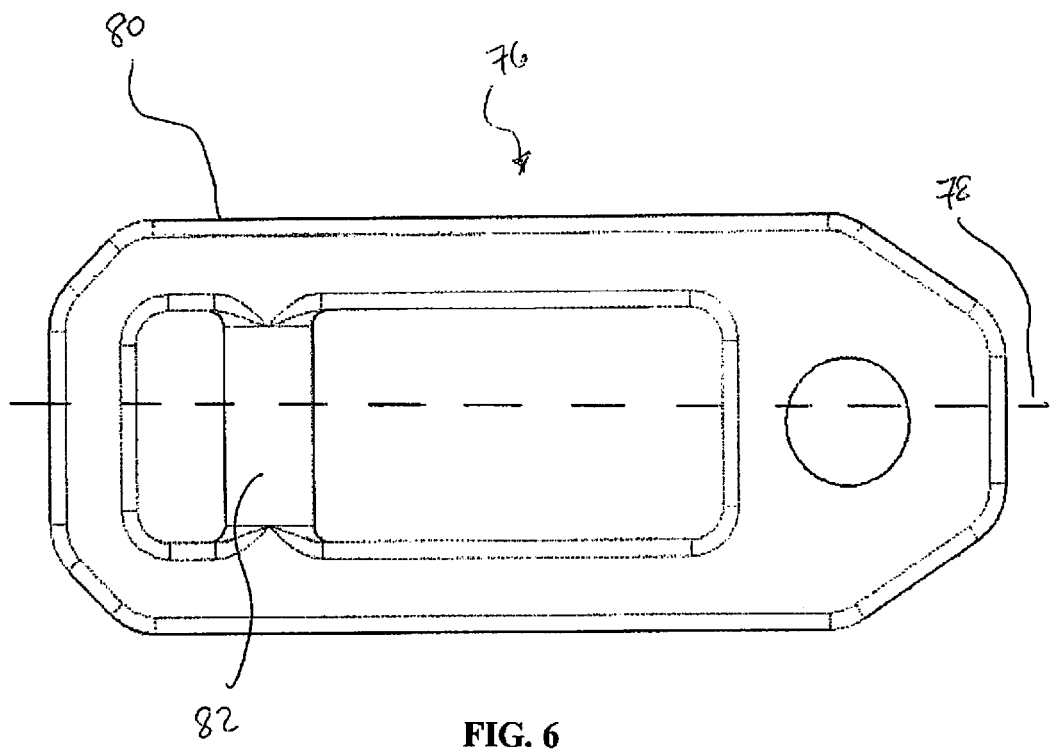
FIG. 6 is an exemplary embodiment of a bone plate of the present invention.

In alternative embodiments, the integrated rod portion may be internal to the outer perimeter of the bone plate. With reference to FIG. 6, bone plate 76 is an elongate body having longitudinal axis 78. Within outer perimeter 80 of bone plate 76, integrated rod 82 is present. One or more apertures (not shown) may be located within different areas of the bone plate.

As one of skill in the art would understand, any number of different configurations may be used to design a bone plate capable of being captured with an integrated rod. Thus, the present invention contemplates bone plates having one or more integrated rods. In the various embodiments, the bone plate may have one, two, or more than two integrated rods located at one or both ends of the bone plate body. Furthermore, the integrated rods may extend in any direction from the bone plate and may extend external to or interior of the outer perimeter of the bone plate.

Furthermore, the bone plate of the present invention contemplates the use of apertures for receiving bone anchors to lag the plate to the bony structure. Any number of different configurations and design may be used with respect to the number and location of apertures on a bone plate. Typically, at least one aperture is present on an end of the bone plate other than the end on which an integrated rod is present. Although is some embodiments, more integrated rods may serve as the sole attachment points for the bone plate.

Depending on the use of the bone plate, the relative position of the integrated rod and apertures (if present) may be important. For example, if used to stabilize vertebral bodies, the bone plate may be configured such that the position of the integrated rod or rods and apertures have certain features such as low profile, conformance of the lower surface of the plate to the bony structures, ability to capture in a first position with maximal access to area being treated, ability to rotate to a second position without anatomical interference, etc.

Figure 7:
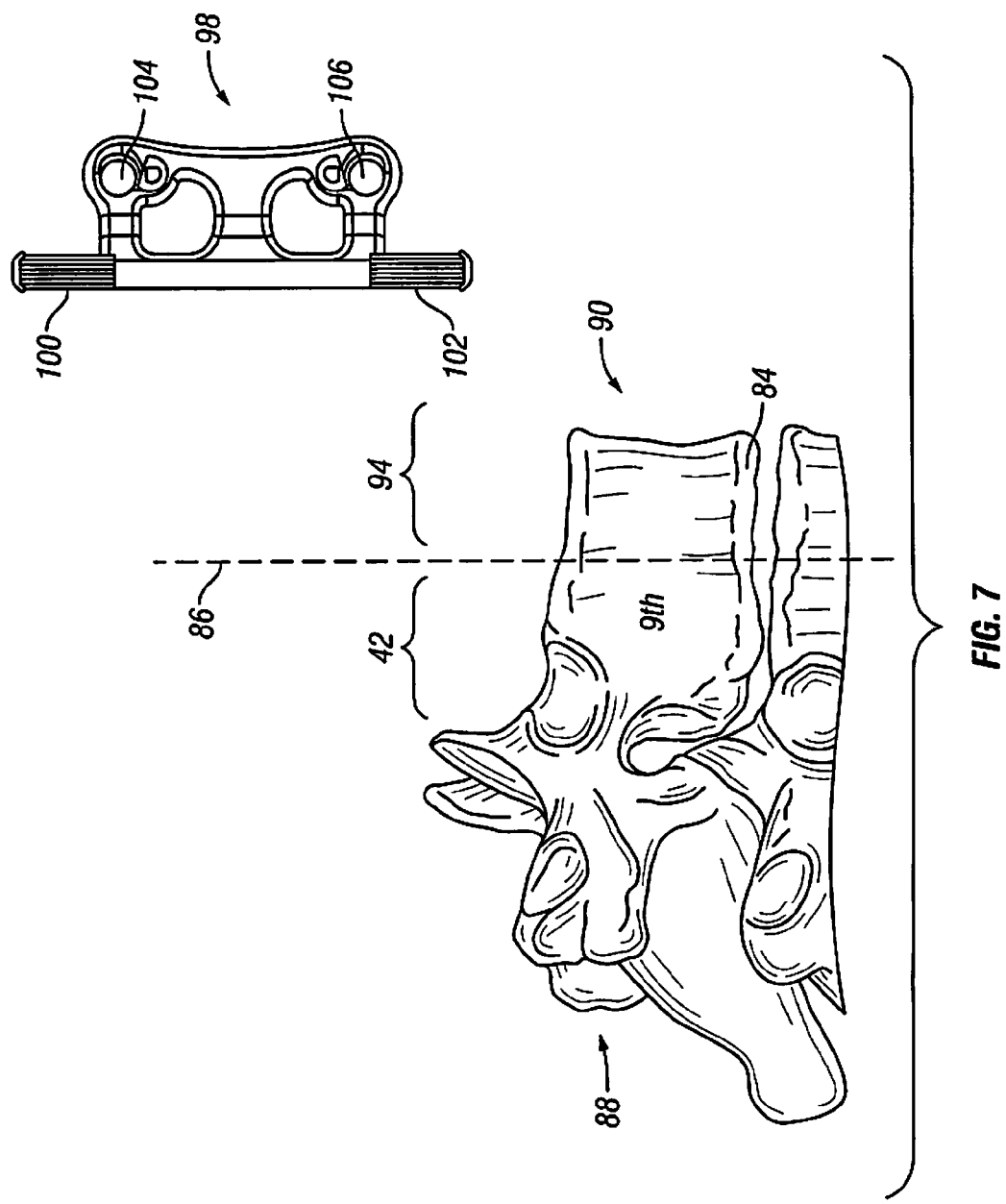
FIG. 7 is a perspective view of the bone plate of FIG. 1 in relation to an illustration of a vertebral body.

With reference to FIG. 7, vertebral body 84 is shown from a lateral perspective. For purposes of discussion only, vertebral body 84 can be referred to as having a midline axis 86 that runs from in a proximal-distal direction. As one of skill in the art would understand, in this orientation, the spine has a posterior side 88 and anterior side 90. Thus with respect to vertebral body 84, reference may be made to a posterior aspect 92 of vertebral body 84 and an anterior aspect 94 of vertebral body 84.

With continuing reference to FIG. 7, bone plate 98 may be configured with integrated rods 100 and 102 and apertures 104 and 106 to meet the aforementioned objectives. Toward that end, in one embodiment, integrated rod portion 102 is positioned on bone plate 98 to fit on posterior aspect 92 of vertebral body 84. Aperture 106 are correspondingly formed to fit on anterior aspect 94 of vertebral body 84. Thus, integrated rod portions 100 and 102 may be attached to attachment points on the surface of vertebral bodies and said attachment points will be generally on a posterior aspect of the vertebral bodies. Similarly, bone fasteners may be inserted through apertures 104 and 106 of bone plate 98 into attachment points located on a generally anterior aspect of the vertebral bodies. In this fashion, bone plate 98 is configured to be captured in a first position that allows access to the treated area. Bone plate 98 is further capable of being rotated to a second position for fixation of the bone plate and stabilization of the bony structures.

Figure 8:
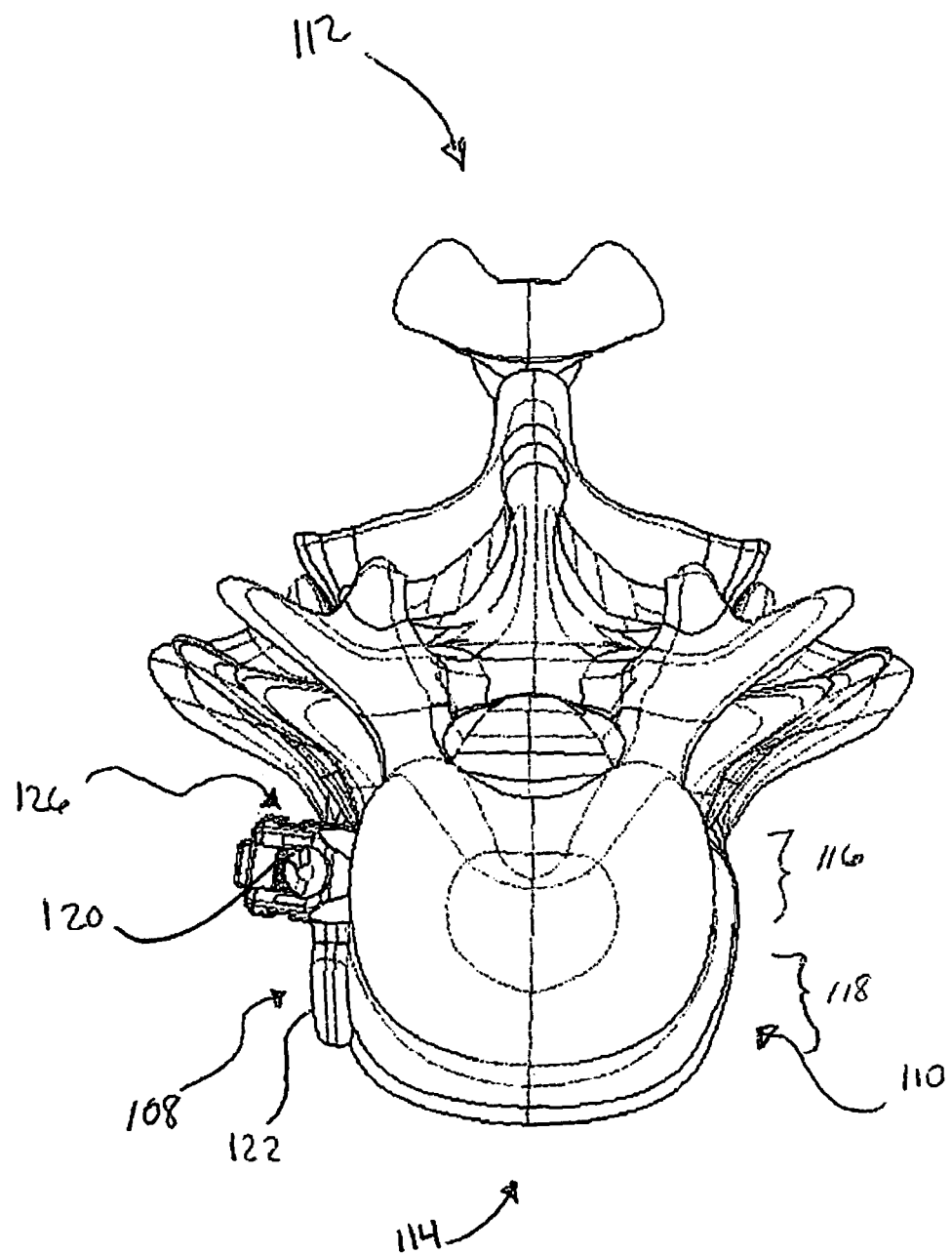
FIG. 8 is a top view of a bone plate attached to a vertebral body.

With reference to FIG. 8, bone plate 108 is shown in a top view relative to vertebral body 110. As seen in this orientation, vertebra 110 has a posterior side 112 and anterior side 114. Thus, as described previously, vertebral body 110 has a posterior aspect 116 and anterior aspect 118. As seen in FIG. 8, bone plate 108 is configured such that integrated rod portion 120 is located on the posterior aspect 116 of vertebral body 110. As further seen in FIG. 8, aperture 122 is located on the anterior aspect 118 of vertebral body 110. Finally, FIG. 8 shows a bone anchor with receiving member 126 inserted into vertebral body 110 at an attachment point on a posterior aspect 116 of vertebral body 110. Bone anchor with receiving member 126 is shown with the integrated rod portion 120 captured and in a second position.

Figure 10:
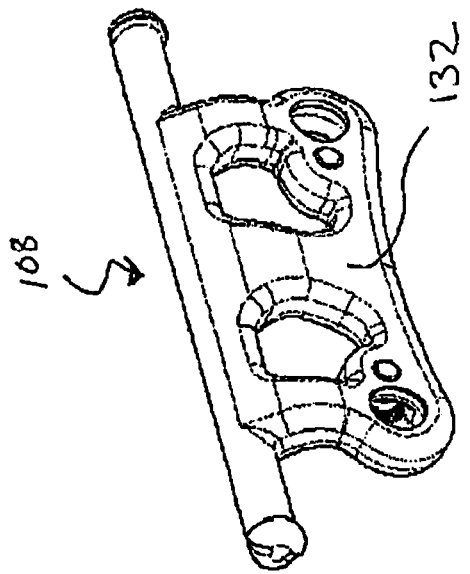
FIG. 10 is an angled perspective view of the bone plate of FIG. 1.
Figure 11:
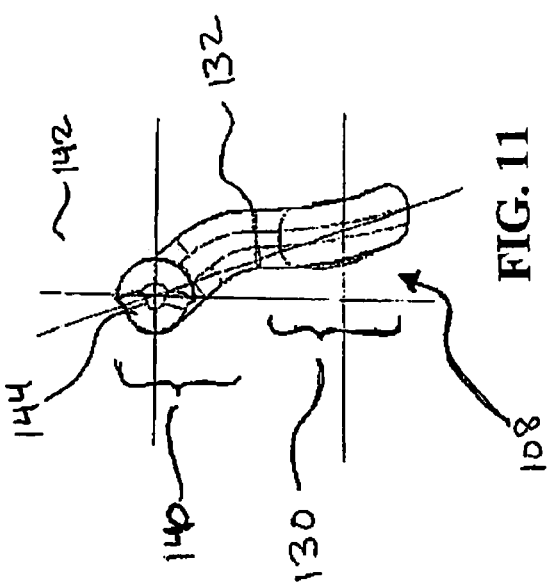
FIG. 11 is a side view of the bone plate of FIG. 1.
Figure 9:
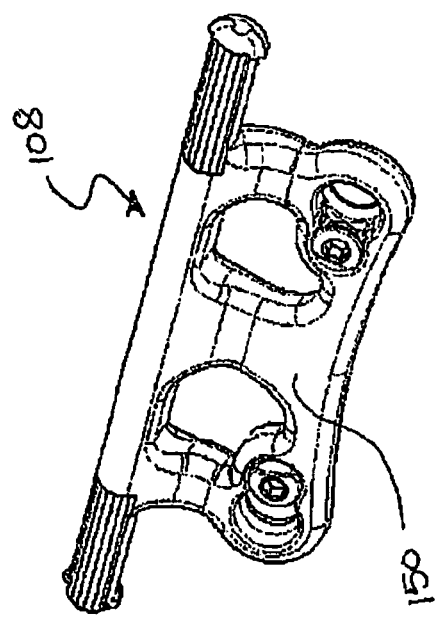
FIG. 9 is an angled perspective view of the bone plate of FIG. 1.

With continuing reference to FIG. 8, bone plate 108 may be shaped to conform with the bony structure to which it is attached. As seen in FIG. 8, portions of lower surface 124 of bone plate 108 may be curved to generally conform to the curvature of vertebral body 110. Other portions of lower surface 124 are curved to attachment of bone anchor with receiving member 126. With reference to FIGS. 9, 10, and 11, bone plate 108 is illustrated from various angles. As seen in FIG. 11, anterior portion 130 of lower surface 132 of bone plate 108 has a concave curvature. This curvature is designed to generally match the curvature of a vertebral body. Depending on the area of the spine to which the bone plate is attached, the exact degree of curvature may vary. As further seen in FIG. 11, posterior portion 140 of bone plate 108 is offset from a midline axis 142. This results in a raised integrated rod portion 144, such that upon seating of the bone plate 108 against a vertebral body, the integrated rod portion 144 is raised above the surface of the bone to accommodate a bone anchor with a receiving member. FIG. 9 is a perspective angled view of bone plate 108 primarily showing the curvature of upper surface 150. FIG. 10 is a perspective angled view of bone plate 108 primarily showing the curvature of lower surface 132. The various curvatures permit the bone plate to have a low profile in a second position as well as allowing access to the treated area in a first position. As one of skill in the art would understand, various curvatures of the surfaces of a bone plate may vary depending on the surface of the bony structures being stabilized.

Figure 12:
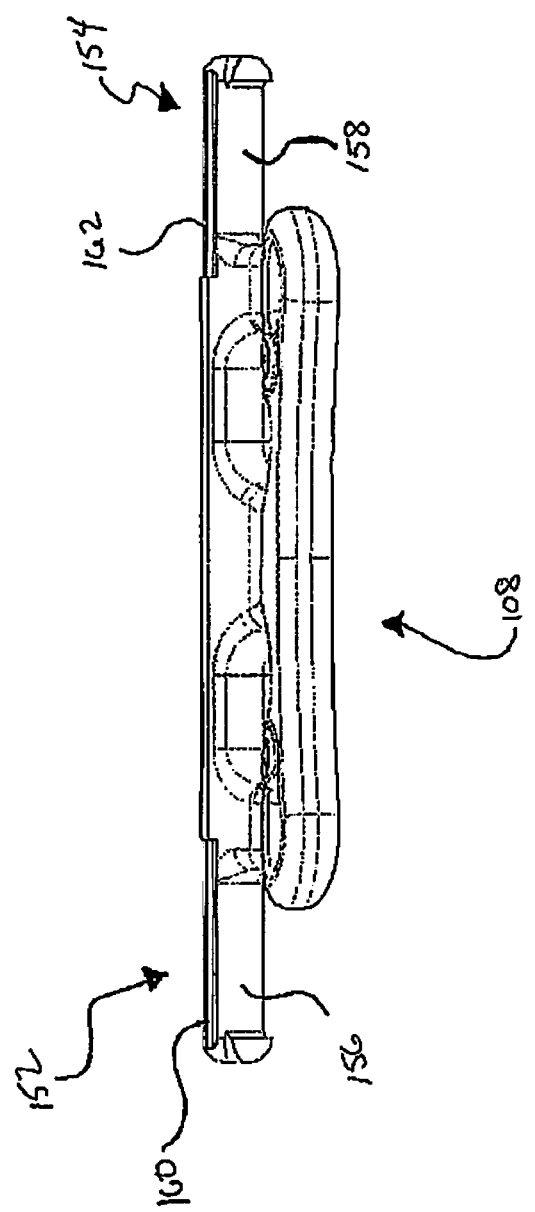
FIG. 12 is a perspective view of the bone plate of FIG. 1.

With reference to FIG. 12, bone plate 108 is shown. As seen in FIG. 12, integrated rod portions 152 and 154 are generally cylindrical. Integrated rod portions may also have a flat portion 156 and 158. Flat portions 156, 158 of integrated rod portions 152 and 154, respectively, are designed to match or providing a mating surface for the receiving member of the bone anchor. In addition, other areas of integrated rod portions 152 and 154 may be configured with a textured surface. With continuing reference to FIG. 12, integrated rod portions 152 and 154 may be configured with a textured surfaces 160 and 162. Textured surfaces 160 and 162 provide bone anchor with receiving member a roughened surface to aid in capture and locking of integrated rod portions 152 and 154.

Figure 13:
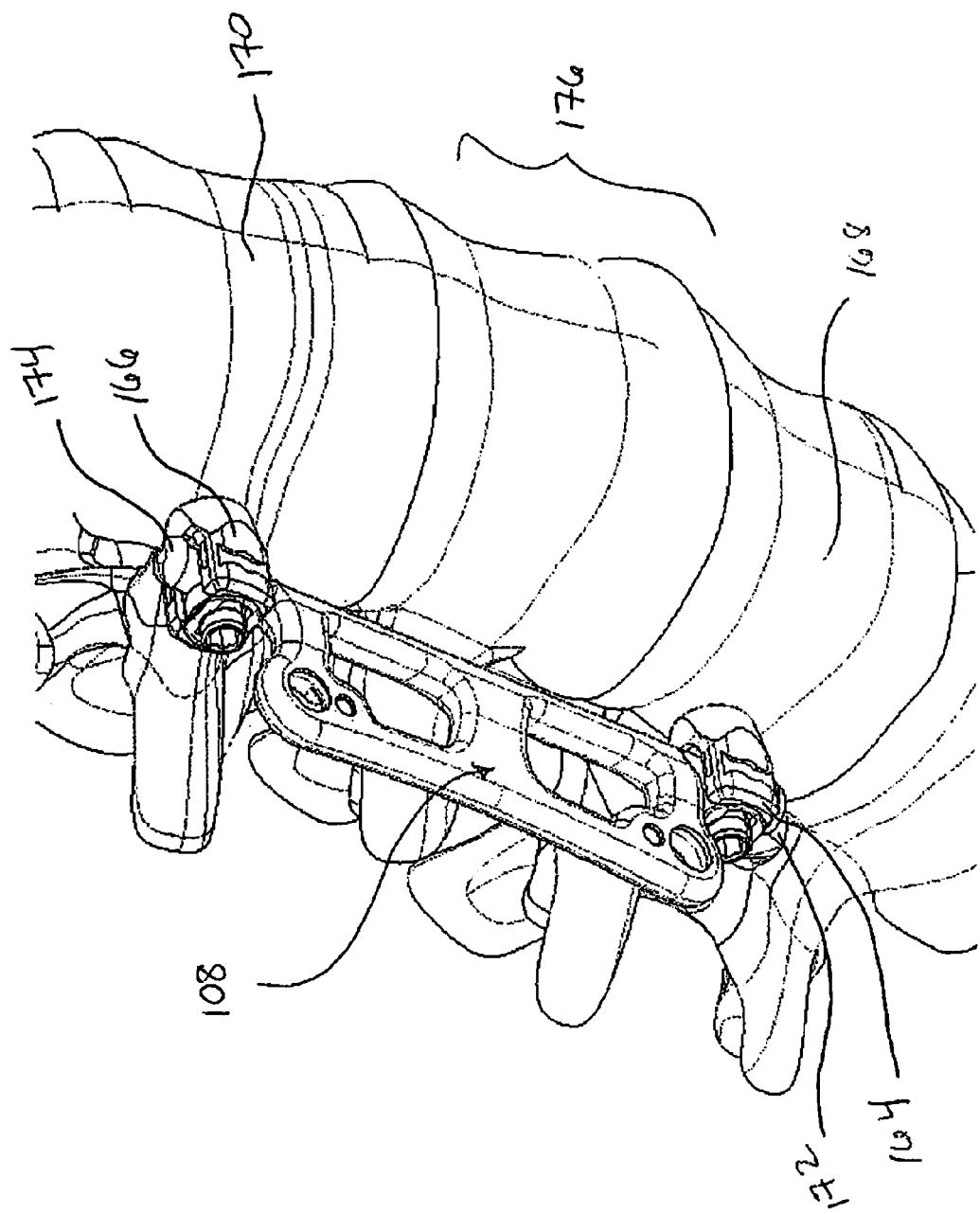
FIG. 13 is a perspective view of the bone plate of FIG. 1 in a first position on vertebral bodies.

With reference to FIG. 13, bone plate 108 is shown in a first position. As seen in FIG. 13, bone plate 108 has been captured by bone anchors with receiving members 164 and 166. More particularly, bone anchors with receiving members 164 and 166 have been inserted into vertebral bodies 168 and 170 at posterior aspect points on the lateral side of the vertebral bodies. Integrated rod portions 172 and 174 have been captured by receiving members of bone anchors. In this first position, the bone plate provides access to treated area 176 of the spine.

Figure 14:
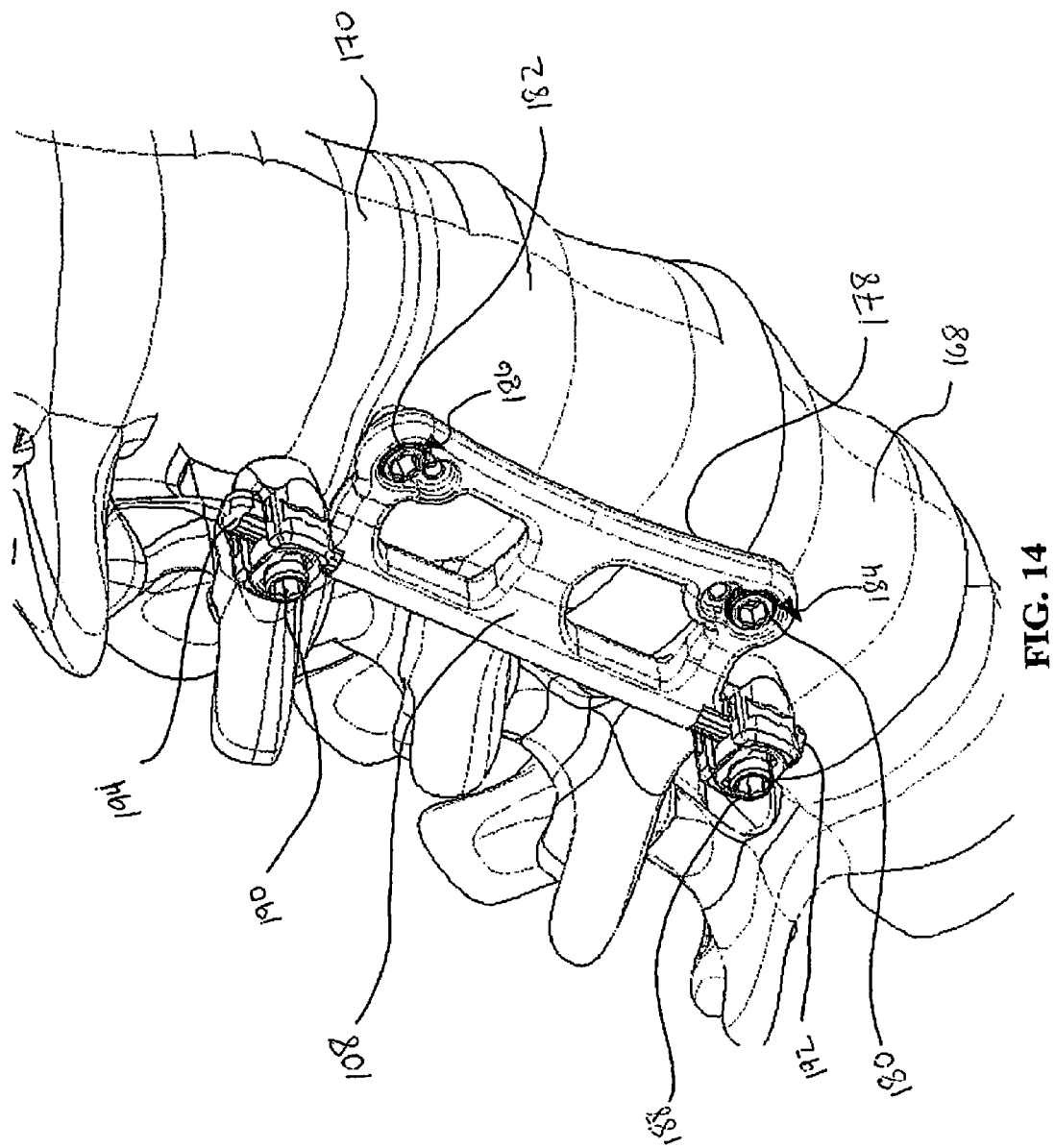
FIG. 14 is a perspective view of the bone plate of FIG. 1 in a second position on vertebral bodies.

With reference to FIG. 14, bone plate 108 is shown in a second position. As seen in FIG. 14, bone plate 108 has been rotated to a second position. In this position, lower surface 178 of bone plate 108 matches or is adjacent the bony surface of vertebral bodies 168 and 170. Bone anchors 180 and 182 have been inserted into apertures 184 and 186. Additionally, set screws 188 and 190 may lock integrated rod portions 192 and 194 into their final positions.

As one of skill in the art would understand, the bone plate may be designed with different lengths to accommodate a variety of uses. For example, with reference to a bone plate used to stabilize vertebral bodies of the spine, bone plates may come in different sizes to span a number of vertebrae. Thus, bone plates may be used for corpectomies involving one, two, or more than two discs. In this way, the bone plate of the present invention can span multiple levels of the spinal column. When the bone plate is attached to vertebral bodies closest to the vertebral body excised in a corpectomy, the remaining vertebral bodies can be said to be adjacent to each other. In some instances, attachment of the bone plate may be preferably made to non adjacent vertebral bodies. This may occur in any number of instances, one of which may be the determination that one or more adjacent vertebral bodies are sufficient healthy for attachment. Thus, in the case of a corpectomy resulting in the excision of one vertebral body, a bone plate spaning three vertebral bodies may be used for attachment a first vertebral body and a third vertebral body.

The bone plate of the present invention may be made of any material suitable for the stabilization of bony structures. In one embodiment, the bone plate is made of titanium; titanium does not elicit an adverse response from a patient's immune system and is a strong, stable, and durable material. In other embodiments, PEEK or other suitable composite materials may be used.

The bone plate of the present invention may also contain radiomarkers to detect orientation and position of the bone plate after implantation. In this configuration, the bone plate may be formed with observable features such as an aperture, bar, or other feature that is clearly distinguishable on a radiogram of the treated area. In this fashion, diagnostic and follow-up procedures may allow for the rapid determination of position.

What is claimed is:

1. A bone plate assembly for stabilizing at least two bony structures, comprising:
   an elongate plate body having a plate portion and first and second integrated rod portions, the plate portion having first and second ends, the elongate plate body having a longitudinal axis extending from the first end to the second end of the plate portion, the first integrated rod portion extending in a first direction away from a center of the plate portion and beyond the first end along a direction parallel to the longitudinal axis and the second integrated rod portion extending in a second direction, opposite to the first direction, away from the center of the plate portion and beyond the second end along a direction parallel to the longitudinal axis, the elongate plate body further comprising a first aperture and a second aperture, the elongate plate body further comprising a fully enclosed first window and a fully enclosed second window, wherein the first window is larger than the first aperture and the second window is larger than the second aperture;
   a first bone fastener having a first receiving member and a second bone fastener having a second receiving member, wherein the first receiving member captures the first integrated rod portion and the second receiving member captures the second integrated rod portion of the elongate plate body, and
   a first bone screw and a second bone screw, wherein the first bone screw is configured to be inserted into the first aperture and the second bone screw is configured to be inserted into the second aperture,
   wherein the first window and the second window extend from an upper surface of the elongate plate body to a lower surface of the elongate plate body,
   wherein along the longitudinal axis, the first window is offset from the first aperture and the second window is offset from the second aperture.

2. The bone plate assembly of claim 1, wherein upon capture of the first and second integrated rod portion by the first bone fastener and second bone fastener, the elongate plate body is movably positionable between a first position and a second position.

3. The bone plate assembly of claim 2, wherein in the first position the elongate plate body provides access to an intervertebral space and wherein in the second position the elongate plate body is orientated to provide maximum stabilization between said two bony structures.

4. The bone plate assembly of claim 3, wherein upon positioning of said elongate plate body in the second position, said lower surface of the elongate plate body is substantially adjacent to the surface of the bony structures.

5. The bone plate assembly of claim 4, wherein the lower surface of said elongate plate body is configured to generally match the curvature of the bony structures to which it is attached.

6. The bone plate assembly of claim 5, wherein said bony structures are vertebral bodies.

7. The bone plate system of claim 1, wherein after the first bone screw and the second bone screw are inserted into the elongate plate body, the elongate plate body is capable of compression and distraction relative to the bony structure.

8. The bone plate system of claim 1, wherein the receiving member of the first fastener and second fastener is capable of locking the integrated rod portion into a generally fixed position relative to the first fastener and second fastener.

9. The bone plate system of claim 1, wherein the first and second integrated rod portions are located at one end of the elongate plate body and the first and second aperture are located at a second end of the elongate plate body.

10. The bone plate system of claim 9, wherein the first and second integrated rod portions are configured to be positioned on a posterior aspect of a vertebral body and the first and second apertures for receiving the first and second bone screw are configured to be positionable on an anterior aspect of the vertebral body.

11. The bone plate system of claim 9, wherein said bony structures are vertebral bodies.

12. The bone plate system of claim 1, wherein each end of the elongate plate body contains an integrated rod portion for attachment to said bony structures.

13. The bone plate system of claim 12, wherein said boney structures are first and second adjacent vertebral bodies.

14. The bone plate system of claim 12, wherein said boney structures are first and second non-adjacent vertebral bodies.

15. The bone plate system of claim 1, wherein the first and second bone fasteners and the first and second bone screws do not extend through the first and second windows.

16. A bone plate assembly for stabilizing at least two bony structures, comprising:
   an elongate plate body having a plate portion and first and second integrated rod portions, the elongate plate body having a longitudinal axis extending from a first end to a second end of the plate portion, the integrated rod portions extend beyond the first and second ends of the plate portion in a direction parallel to the longitudinal axis, wherein the first integrated rod portion extends in a first direction away from a center of the plate portion and the second integrated rod portion extends in a second direction, opposite to the first direction, away from the center of the plate portion;
   a first bone fastener and a second bone fastener, the first and second bone fasteners comprise a first receiving member and a second receiving member, respectively, to capture first and second portions of the integrated rod portion of the plate body,
   the plate body further defining at least a first aperture and a second aperture and
   a first bone screw is configured to be threaded into a first vertebral body thereby moving the bone plate directly into contact with said first vertebral body and a second bone screw is configured to be threaded into a second vertebral body thereby moving the bone plate directly into contact with said second vertebral body, wherein the elongate plate body has a length such that it is attachable to different vertebral bodies, wherein the elongate plate body further comprises a first window and a second window, wherein the first window and the second window extend from an upper surface of the elongate plate body to a lower surface of the elongate plate body, wherein the first window is independent from the second window and wherein the first window is larger than the first aperture and the second window is larger than the second aperture, wherein along the longitudinal axis, the first window is offset from the first aperture and the second window is offset from the second aperture.

17. The bone plate system of claim 16, wherein the integrated rod portion has a textured surface.

18. The bone plate system of claim 16, wherein the first and second windows are asymmetrical about a longitudinal axis.

19. The bone plate system of claim 16, wherein the first and second bone fasteners and the first and second bone screws do not extend through the first and second windows.

20. A bone plate assembly for stabilizing at least two bony structures, comprising:

an elongate plate body having a plate portion, the plate portion having first and second ends, the elongate plate body having a longitudinal axis extending from the first end to the second end of the plate portion, the elongate plate body further comprising a first aperture and a second aperture, the elongate plate body further comprising a fully enclosed first window and a fully enclosed second window, wherein the first window is larger than the first aperture and the second window is larger than the second aperture, wherein the first window and the second window extend from an upper surface of the elongate plate body to a lower surface of the elongate plate body;

a rod portion including a first integrated rod portion, a central rod portion, and a second integrated rod portion, wherein the first integrated rod portion extends beyond the first end along a direction parallel to the longitudinal axis, the central rod portion is integral with the plate portion, and the second integrated rod portion extends beyond the second end along a direction parallel to the longitudinal axis;

a first bone fastener having a first receiving member and a second bone fastener having a second receiving member, wherein the first receiving member captures the first integrated rod portion and the second receiving member captures the second integrated rod portion of the elongate plate body; and a first bone screw and a second bone screw, wherein the first bone screw is configured to be inserted into the first aperture and the second bone screw is configured to be inserted into the second aperture, wherein along the longitudinal axis, the first window is offset from the first aperture and the second window is offset from the second aperture.

* * * * *